(12) United States Patent
Arsiwalla et al.

(10) Patent No.: US 10,362,772 B2
(45) Date of Patent: Jul. 30, 2019

(54) METHOD AND SYSTEM FOR BREEDING INSECTS, USING A PLURALITY OF INDIVIDUAL CRATES

(71) Applicant: Bühler Insect Technology Solutions AG, Uzwil (CH)

(72) Inventors: Tarique Arsiwalla, Amsterdam (NL); Kees Wilhelmus Petrus Aarts, Amsterdam (NL)

(73) Assignee: Bühler Insect Technology Solutions AG, Uzwil (CH)

( * ) Notice: Subject to any disclaimer, the term of this patent is extended or adjusted under 35 U.S.C. 154(b) by 624 days.

(21) Appl. No.: 14/785,452

(22) PCT Filed: Apr. 17, 2014

(86) PCT No.: PCT/NL2014/050247
§ 371 (c)(1),
(2) Date: Oct. 19, 2015

(87) PCT Pub. No.: WO2014/171829
PCT Pub. Date: Oct. 23, 2014

(65) Prior Publication Data
US 2016/0066552 A1 Mar. 10, 2016

(30) Foreign Application Priority Data
Apr. 19, 2013 (NL) ...................... 2010666

(51) Int. Cl.
*A01K 67/033* (2006.01)
*A01K 29/00* (2006.01)

(52) U.S. Cl.
CPC .......... *A01K 67/033* (2013.01); *A01K 29/005* (2013.01); *A01K 67/0332* (2013.01); *A01K 2267/00* (2013.01)

(58) Field of Classification Search
CPC ... A01K 67/04; A01K 67/033; A01K 67/0332
(Continued)

(56) References Cited

U.S. PATENT DOCUMENTS 5,351,643 A * 10/1994 Hughes ................ A01K 67/033
119/6.5
5,819,685 A * 10/1998 Kappelt ............... A01K 67/033
119/6.5

(Continued)

FOREIGN PATENT DOCUMENTS

EP 2703372 A4 * 10/2014 .......... A01K 67/033
KR 100524413 B1 11/2005

(Continued)

*Primary Examiner* — Monica L Williams
*Assistant Examiner* — Aaron M Rodziwicz
(74) *Attorney, Agent, or Firm* — The Webb Law Firm

(57) ABSTRACT

A method and system for breeding insects, using a plurality of individual crates, wherein at least a portion of each crate is filled with a substrate, containing feed stock, and immature phases of insects. Also provided is a climate area housing the crates that has an aeration system. A conveyor system is included in the system for retrieving crates from the climate area and for returning same thereto. An observation system for obtaining observations, including data and measurements, and downstream thereof a feedstock supply station are arranged along the conveyor system. The method includes steps of aerating the substrate and the immature phases of insects with the aeration system, when in the climate area; periodically retrieving at least one individual crate of the plurality of crates by the conveyor system from the climate area and passing it to the observation system; obtaining an observation of the substrate and the immature phases of insects in the at least one retrieved crate; and interpreting the observation of a retrieved individual crate and determining one of a requirement for adding an amount of supplementary feed stock, and a reason to withdraw the (Continued)

insects from further breeding for harvesting or discarding from further breeding. The method and system are further arranged for returning the retrieved individual crate to the climate area via the feedstock supply station, when a required amount of supplementary feedstock has been determined, and transferring the retrieved individual crate to one of an area for harvesting and an area for discarding, when a reason for withdrawal has been determined. The steps of the method are repeated for as long as at least one of the plurality of crates remains in the climate area.

4 Claims, 3 Drawing Sheets

(58) Field of Classification Search
USPC .......................................................... 119/6.5
See application file for complete search history.

(56) References Cited

U.S. PATENT DOCUMENTS

| | | | |
|---|---|---|---|
| 9,302,949 B2* | 4/2016 | Milin | C05F 17/0009 |
| 9,462,795 B2* | 10/2016 | Chin | A01K 67/033 |
| 9,629,339 B2* | 4/2017 | Newton | A01K 29/00 |
| 2010/0129273 A1* | 5/2010 | Milin | C05F 17/0009 |
| | | | 422/187 |
| 2011/0167721 A1* | 7/2011 | Lejeune | A01H 1/04 |
| | | | 47/65 |
| 2013/0319334 A1* | 12/2013 | Newton | A01K 67/033 |
| | | | 119/6.5 |

FOREIGN PATENT DOCUMENTS

| | | |
|---|---|---|
| WO | 9301711 A1 | 2/1993 |
| WO | 9419296 A1 | 9/1994 |
| WO | 2012073949 A1 | 6/2012 |
| WO | 2012115959 A2 | 8/2012 |

* cited by examiner

US 10,362,772 B2

METHOD AND SYSTEM FOR BREEDING INSECTS, USING A PLURALITY OF INDIVIDUAL CRATES

CROSS-REFERENCE TO RELATED APPLICATIONS

This application is the United States national phase of International Application No. PCT/NL2014/050247 filed Apr. 17, 2014, and claims priority to The Netherlands Patent Application No. 2010666 filed Apr. 19, 2013, the disclosures of which are hereby incorporated in their entirety by reference.

BACKGROUND OF THE INVENTION

Field of the Invention

The invention relates to a method, system for breeding insects, and a breeding container for use in the method and system. The invention also relates to waste conversion.

Description of Related Art

From the published international patent application document WO 2012/115959 A2 it is known for a larvae rearing system to have a plurality of open topped culture trays arranged in stacks, with each tack comprised of multiple levels of trays. A feed delivery system automatically delivers larval feed to selected culture trays, while a separate water delivery system delivers water to the culture trays.

In a system for breeding flies and decomposing organic waste, as disclosed in Korean patent document KR 100524413 B1, successive breeding chambers are used for breeding imagoes of house fly and for diptera parasitoids. Each breeding chamber uses a plurality of breeding containers held in stacked rows by a mounting frame.

The use of individual containers or trays in the treatment of organic matter and/or the breeding of insects is further described in patent documents U.S. Pat. Nos. 5,819,685, 5,351,643, WO 2012/073949, WO 93/01711, and WO 94/19296.

In the known systems it has not been possible to continuingly observe the processes in the individual containers in an efficient manner. This has reduced control over the processes and sometimes caused erratic yields.

Accordingly it is an object of the present invention to propose and offer an improved system and method for breeding insects. In a more general sense it is thus an object of the invention to overcome or ameliorate at least one of the disadvantages of the prior art. It can also be seen as an object of the present invention to provide alternative structures and method steps that are less cumbersome in assembly and operation and which moreover can be accomplished relatively inexpensively. Alternatively it is an object of the invention to at least provide the public with a useful choice.

SUMMARY OF THE INVENTION

To this end the invention provides a method for breeding insects, a system for performing the method, and a crate for use in the method and system as defined by one or more of the appended claims.

The invention is useful for producing insects, in particular in their larval or pupal stage, and worms for conversion into nutrient material, such as proteins, fatty acids, chitin, or like.

More in particular the invention is useful in providing basic matter to be fully converted into several nutrient streams, such as fat-containing, aqueous-containing and solid-containing fractions. Such an efficient converting method, which is not part of the present invention, can comprise the steps of:

(a) squashing insects or worms thereby obtaining a pulp,
(b) heating the pulp to a temperature of 70-100° C., and
(c) subjecting the heated pulp to a physical separation step.

The physical separation step, may include decanting and/or centrifuging. Such a method may optionally also comprise enzymatic treatment of the pulp, such as enzymatic hydrolysis for obtaining a hydrolysed mixture prior to the heating step. A fat-containing fraction obtained by such methods can comprise at least 80 wt. % insect or worm fat of which at least 40 wt. % can be saturated fats. An aqueous protein fraction can be dried to obtain dried protein material, which may contain at least 40 wt. % insect or worm protein-derived matter and at most 25 wt. % insect or worm fat based on dry weight. The protein can then have a pepsin digestibility of at least 50%. The resulting nutrient streams can be used in food, feed and pharmaceutical industry.

BRIEF DESCRIPTION OF THE DRAWINGS

Further advantageous aspects of the invention will become clear from the appended description and in reference to the accompanying drawings, in which.

DESCRIPTION OF THE INVENTION

Figure 1:
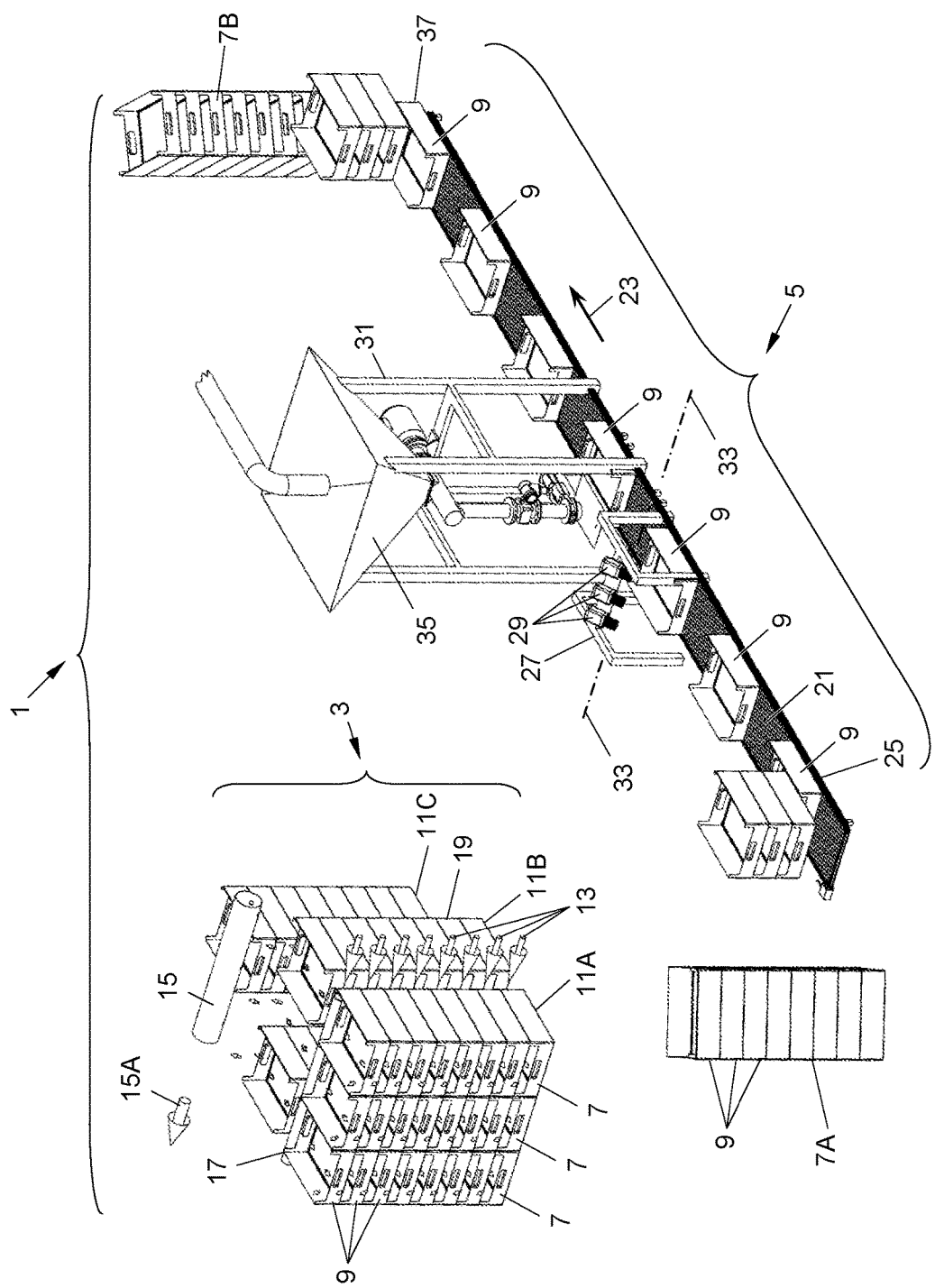
FIG. 1, in a birds eye perspective, schematically shows a production facility for breeding insects in accordance with the present invention.

In FIG. 1 a production facility is shown in the form of an insect breeding system 1. The insect breeding system 1 includes a climate area 3 and a feed area 5. In the climate area columns 7 of stacked individual crates 9 are arranged in a plurality of parallel rows 11A, 11B, 11C. For simplification FIG. 1 only shows a limited number of stacked columns 7, and a limited number of parallel rows 11A-C. It should however be understood that preferably and advantageously a great many of stacked columns 7 and rows 11A-C will be present in an actual production facility. The adjacent rows 11A-C are spaced from one another to allow an aeration system to supply conditioned air between a first pair of adjacent rows 11A, 11B, and to withdraw used air from between an adjacent second pair of rows 11B, 11C. The supply of conditioned air is indicated by arrows 13 and the withdrawal of used air is represented by a suction tube 15 and arrow 15A.

For the supply and discharge of air other ways to pass the air between the crates are also conceivable. In the climate area 3 the successive rows 11A-11C are repeated such that the supply and withdrawal of air alternates at each corridor 17,19 between adjacent pairs of rows 11A-11C. In the feed area 5 a conveyor 21 for moving individual crates 9, moves in a direction indicated by arrow 23. A retrieved column 7A of stacked individual crates 9 is offered to a destacker unit 25, which destacks the stacked columns into individual creates. Each individual crate 9 then passes into an observation station 27. The observation station 27 includes a weighing scale (not shown, but conventional) to obtain the weight of an individual crate 9 including its substrate and insect content and optionally an RFID identification unit for assigning data and measurements obtained by the observation station to a central control unit (not shown, but conventional). The observation station 27 further includes a camera 29 for obtaining an image of the contents of each individual crate 9 passing the observation station 27. The observation station 27 can include a multitude of camera systems (laser, sick range, IR, heat scan etc). The observation station 27 functions as an observation station at crate level. The acquired data is interpreted by a central control unit (not shown, but conventional) to determine a requirement for adding an appropriate amount of supplementary feed stock, or to determine a reason to withdraw the individual crate 9 from further breeding. Other options as a result of the interpretation of the acquired data are also conceivable. A reason to withdraw an individual crate 9 from further breeding may be an indication from the preceding observation that its contents is ready for harvesting, but also that its contents is beyond recovery and needs to be discarded. Withdrawal of an individual crate 9 to prevent it from progressing to a feed station 31 may be performed manually, but may also be performed automatically by robot or other means. In case withdrawal of crates 9 from between the observation station 27 and the feed station 31 is performed automatically, the conveyor 21 may also be joined by a further conveyor at an intersection indicated by line 33.

At the feed station 31 feed stock, contained in a hopper 35, usually consisting of waste material, is dosed in amounts determined individually by a central control unit (not shown, but conventional) to each of the crates 9 requiring additional feed stock. After leaving the feed station 31 each individual retrieved crate 9 progresses to a restacker 37 where the individual crates 9 are again stacked into a column 7B ready for return to the climate area 3.

While not shown in any detail in FIG. 1, it should be understood that the retrieved column 7A, and the column 7B for return to the climate area 3 may also be automatically conveyed between the climate area 3 and the feed area 5 by an appropriate automatic conveying system (not shown, but conventional). Such further conveying systems may also be adapted to rearrange the columns and rows 11A-C within the climate area 3 to obtain a proper first-in-first-out order for the columns of crates. Such conveying systems are well known to the skilled individual and do not require further explanation for the purpose of the present invention.

Figure 2:
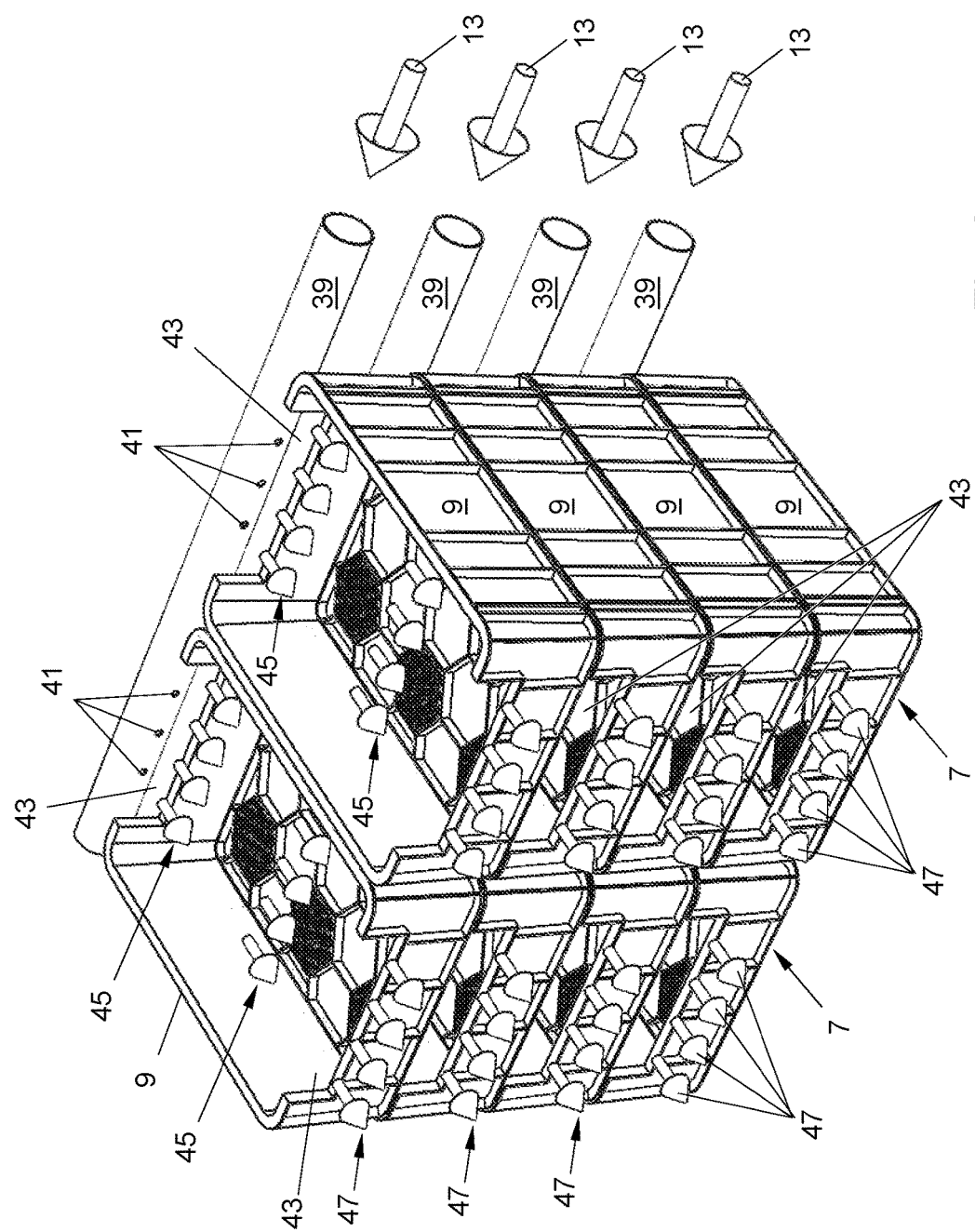
FIG. 2 is a partial perspective view showing a plurality of crates stacked in adjacent columns with an aeration system according to the invention.

In FIG. 2 the aeration of crates 9 in the climate area is shown in greater detail. In this example the aeration system is embodied by a plurality of air manifolds 39, each having evenly spaced outlet openings 41. The manifolds 39 and the outlet openings 41 are each spaced to correspond with end openings 43 created at opposite ends of the crates 9. Conditioned air of a predetermined temperature, humidity, volumetric rate, and/or constitution is fed to the manifolds 39 as indicated by arrows 13. The flow of conditioned air is then guided over a bed of substrate contained in each crate 9 upon leaving the respective outflow openings 41. The outflow openings 41 are aligned with the respective rear end openings 43 of the individual crates 9 and guided over the substrate in the crates 9 as indicated by arrows 45. A surplus of air then leaves the crates 9 through respective front end openings 43 as indicated by arrows 47. While the crates 9 are shown empty in FIG. 2, it will be understood that these will each be filled with an appropriate amount of substrate and insect larvae, when the system is in operation. The used air that leaves the crates 9 in accordance with arrows 47 is collected in the corridor in front of these crates by a suction tube 15 as illustrated in FIG. 1. The air so withdrawn can be analysed, so that its properties may be adjusted as necessary for reuse in the system. Temperature differences between the conditioned air and the withdrawn used air may advantageously benefit energy conservation.

Figure 3:
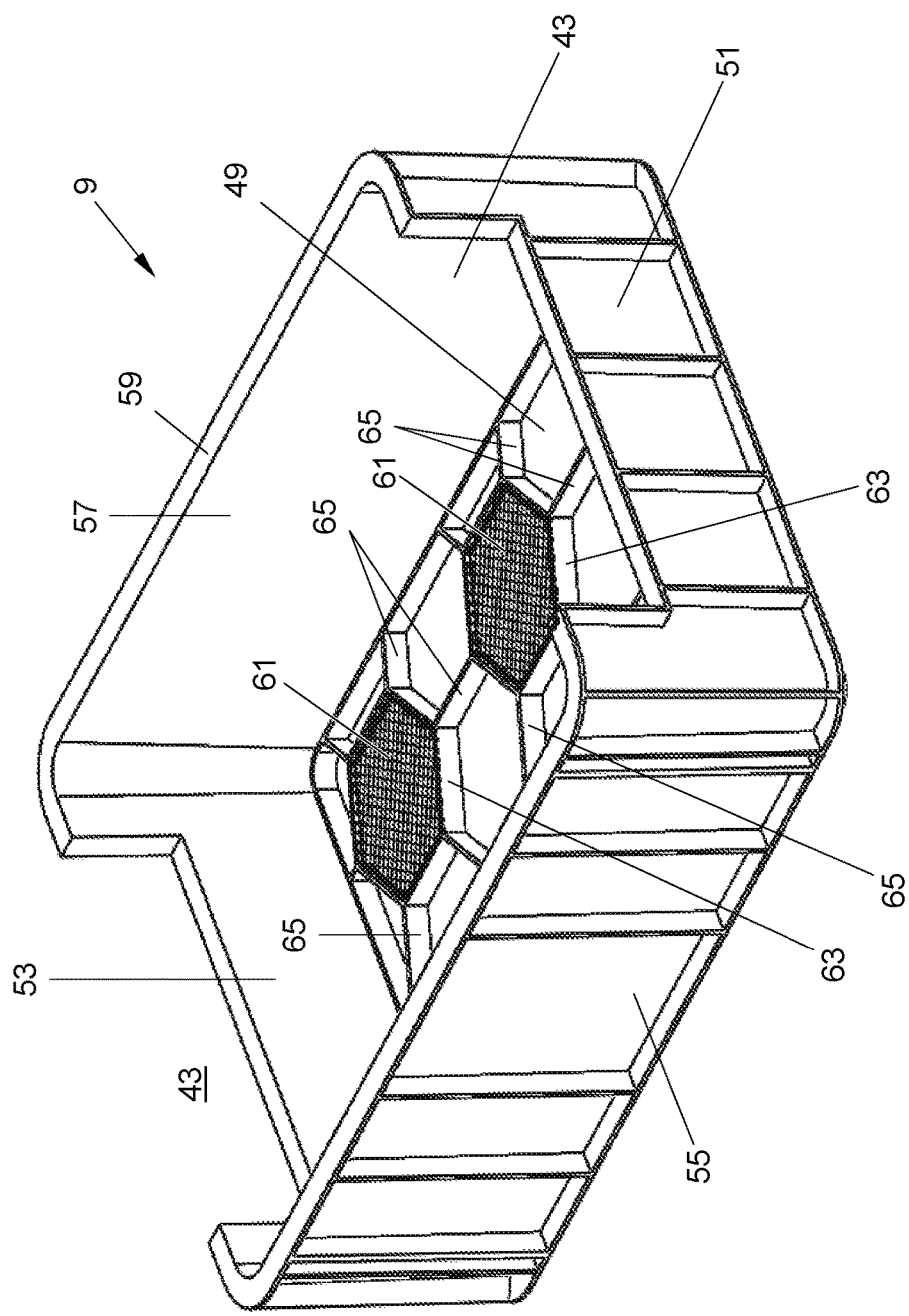
FIG. 3 is a perspective view of an individual crate according to the invention.

In FIG. 3 an individual crate 9 is shown. Each crate 9 includes a generally rectangular bottom 49 having upstanding opposite front and rear walls 51, 53, and opposite side walls 55, 57. As already explained in reference to FIG. 2 the opposite front and rear walls 51, 53 each have one of the end openings 43 formed by a recess in the upper edge 59 at the upstanding front and rear walls 51, 53. The bottom 49 is provided in this example with a limited number of insert receiving openings 61 for receiving an insert, such as a wire mesh shown in FIG. 3. The insert receiving openings 61 are bounded by an upstanding perimeter edge 63 for preventing moisture that is collected on the bottom 49 of the crate 9 to leak from the opening 61 where it could contaminate the contents of another crate that is lower in a stack, when in use. Alternatively the insert receiving opening 61 could be filled with a closed insert or with an insert having a different mesh. When closed with a permeable insert, such as a mesh or filter material, the openings 61 in the bottom 49 of the crates 9 may provide additional aeration of a substrate therein from below. Such an aeration from below results from the forced flow of conditioned air over the substrate of a crate lower in the stack (as indicated by the arrows 45 in FIG. 2). When aeration from below the substrate is not required, then completely closed inserts may be inserted into the openings 61. In such instances it is also conceivable that an alternative crate without insert receiving openings will be used. Conversely when bottom aeration can be standardized it is also conceivable that the mesh covered openings are integrally formed in the bottom of the crate. When more than one insert receiving opening 61 is provided in each crate 9, it is also an option to use a combination of different inserts in one and the same crate. Further it is also seen in FIG. 3 that the upstanding perimeter edges 63 around the openings 61 can also be part of a bottom reinforcing grid 65.

Thus an insect breeding technique has been described, which has been developed for the purpose of large scale insect production. The growth technique is based on an interaction between a specially designed crate and a climate control technique and a working principle, by which the crates hold the insects and substrate which is fed to the insects. The crates are placed in stacks in front of aeration walls and/or tubular manifolds. The aeration walls have openings at the same heights as aeration openings in the crate. This allows for management of an airflow over the insects and substrate. For the supply and discharge of air it is also possible for the space between the stacks to be held at an over-pressure. The air then passes between the openings. Then a system is obtained that does not have openings on the same height, but offering another way to pass the air between the crates. The total production facility then has stacks of crates and crate level climate control. The air is controlled before it is blown over the crate. The air that has passed is sucked away and measured. This way a measurement and control system can monitor how much activity has taken place inside the crate. The climate system can then adjust the air characteristics of the air that is blown over the crate again. This way it becomes possible to maximize the growth potential of the insects in the crates. The total system is designed to generate as much output as possible. The crate is designed to be stackable and has design aspects that allow for optimal climate control of the insects and of a substrate in the crates. The crate can vary in size. For the example as detailed here it can be a crate having a size of 800×600×260 mm (length×width×height). Two sides of the crate are fully closed and two other sides have an opening at the top. The bottom of the crate has several pre-formed openings that allow for inserts of various materials. In the described example the crate has four openings. These openings are made such that inserts can be placed in the opening after production. Such inserts can be closed or preformed plates with wired mesh. The side openings and the bottom inserts can further be used for optimal climate control. The side openings allow for flow over the substrate and underneath the bottom of the crate placed immediately above. The bottom openings also allow for extra oxygen providence and/or for energy off-take. This latter option can be important for specific growth processes whereby a lot of energy is produced and/or when the substrate layers become thicker. Hence the bottom openings offer flexibility by being closeable with plates or plates with various types of wire meshes. Such wire meshes can vary in material, mesh and thickness. The selection of the inserts can be different for various types of insects.

As regards climate control, a climate wall is thus made with openings at the same height as the openings in the crates. The climate wall can be a vertical hollow wall with openings or tubular manifolds suspended at the same height as the crate openings. Air is blown into the wall and/or tubular manifolds and is blown out over the crates. The air that is blown into the wall and/or tubular manifolds can also be regulated in respect of various of its aspects, such as temperature, moist level, energy content, gas content, flow rate and volume, and/or pressure, etc. The air that has been passed through the crates will have changed in composition. Such a change in composition may indicates the amount of activity inside the crates and is a proxy for processes like insect growth, material decay and/or degradation, life cycle progress, etc. The changed values in air composition and quality can then be used to determine the characteristics of the new air that is blown through the wall/tubular manifolds. The entire system of crates and climate control allows for a high-level of automation for large-scale insect production factory lines.

Accordingly there has been described a method and system 1 for breeding insects, using a plurality of individual crates 9, wherein at least a portion of each crate is filled with a substrate, containing feed stock, and immature phases of insects. Also provided is a climate area 3 housing the crates 9 that has an aeration system. A conveyor system 21 is included in the system for retrieving crates 9 from the climate area 3 and for returning same thereto. An observation system 27 for obtaining observations, including data and measurements, and downstream thereof a feedstock supply station 31 are arranged along the conveyor system 21. The method includes steps of aerating the substrate and the immature phases of insects with the aeration system, when in the climate area 3; periodically retrieving at least one individual crate 9 of the plurality of crates by the conveyor system 21 from the climate area 3 and passing it to the observation system 27; obtaining an observation of the substrate and the immature phases of insects in the at least one retrieved crate; and interpreting the observation of a retrieved individual crate and determining one of a requirement for adding an amount of supplementary feed stock, and a reason to withdraw the insects from further breeding for harvesting or discarding from further breeding. The method and system are further arranged for returning the retrieved individual crate 9 to the climate area 3 via the feedstock supply station 31, when a required amount of supplementary feedstock has been determined, and transferring the retrieved individual crate to one of an area for harvesting and an area for discarding, when a reason for withdrawal has been determined. The steps of the method are repeated for as long as at least one of the plurality of crates 9 remains in the climate area 3.

The method and system according to the invention is applicable to many insects which have maggot and/or larval stages. In particular insects such as the House Fly (*musca domestica*), the Black Soldier Fly (*Hermetia Illucens*), and the BowFly can be bred very effectively and efficiently in this system.

It is thus believed that the operation and construction of the present invention will be apparent from the foregoing description and drawings appended thereto. It will be clear to the skilled person that the invention is not limited to any embodiment herein described and that modifications are possible which should be considered within the scope of the appended claims. Also kinematic inversions are considered inherently disclosed and to be within the scope of the invention. In the claims, any reference signs shall not be construed as limiting the claim. The term 'comprising' and 'including' when used in this description or the appended claims should not be construed in an exclusive or exhaustive sense but rather in an inclusive sense. Thus the expression 'comprising' as used herein does not exclude the presence of other elements or steps in addition to those listed in any claim. Furthermore, the words 'a' and 'an' shall not be construed as limited to 'only one', but instead are used to mean 'at least one', and do not exclude a plurality. Features that are not specifically or explicitly described or claimed may be additionally included in the structure of the invention within its scope. Expressions such as: "means for . . . " should be read as: "component configured for . . . " or "member constructed to . . . " and should be construed to include equivalents for the structures disclosed. The use of expressions like: "critical", "preferred", "especially preferred" etc. is not intended to limit the invention. Additions, deletions, and modifications within the purview of the skilled person may generally be made without departing from the spirit and scope of the invention, as is determined by the claims.

The invention claimed is:

1. A system for breeding insects, wherein the system includes:
    a plurality of crates;
    a climate area having an aeration system arranged for accommodating the plurality of crates in the climate area;
    a conveyor system for retrieving crates of the plurality of crates from the climate area;
    an observation system for obtaining observations along the conveyor system;
    a feedstock supply station along the conveyor system, downstream of the observation system;
    at least one aeration wall in the climate area, wherein the at least one aeration wall includes one of a hollow wall and a plurality of tubular manifolds, each being arranged for blowing conditioned air over the substrate in each crate; and
    wherein the observation system includes a camera for obtaining an image of the substrate and insects in each retrieved individual crate, and wherein the obtained image is interpreted to determine one of a requirement for adding an amount of supplementary feed stock, and a reason to withdraw the insects from further breeding for harvesting or discarding from further breeding.

2. The system according to claim 1, wherein the at least one aeration wall includes a plurality of exit openings arranged in a pattern that positions each exit opening in correspondence with individual crates of the columns and rows.

3. A system for breeding insects, wherein the system includes:
a plurality of crates;
a climate area having an aeration system arranged for accommodating the plurality of crates in the climate area;
a conveyor system for retrieving crates of the plurality of crates from the climate area;
an observation system for obtaining observations along the conveyor system;
a feedstock supply station along the conveyor system, downstream of the observation system;
wherein the observation system includes a camera for obtaining an image of the substrate and insects in each retrieved individual crate, and wherein the obtained image is interpreted to determine one of a requirement for adding an amount of supplementary feed stock, and a reason to withdraw the insects from further breeding for harvesting or discarding from further breeding; and
wherein the climate area is arranged to accommodate the plurality of stacked columns of crates in parallel rows, is also arranged to receive two of such rows, separated by a corridor, between opposite aeration walls, wherein the conditioned air after aerating the substrate and the immature phases of insects is collected from the corridor between two rows of columns of crates and said conditioned air is checked for alterations of its properties.

4. A system for breeding insects, wherein the system includes:
a plurality of crates;
a climate area having an aeration system arranged for accommodating the plurality of crates in the climate area;
a conveyor system for retrieving crates of the plurality of crates from the climate area;
an observation system for obtaining observations along the conveyor system;
a feedstock supply station along the conveyor system, downstream of the observation system;
wherein the observation system includes a camera for obtaining an image of the substrate and insects in each retrieved individual crate, and wherein the obtained image is interpreted to determine one of a requirement for adding an amount of supplementary feed stock, and a reason to withdraw the insects from further breeding for harvesting or discarding from further breeding; and
wherein the conveyor system for retrieving crates of the plurality of crates from the climate area is capable of returning said crates of the plurality of crates to the climate area.

* * * * *